United States Patent
Ikeguchi et al.

(10) Patent No.: US 8,974,796 B2
(45) Date of Patent: Mar. 10, 2015

(54) AGENT FOR PREVENTING ADVERSE SIDE EFFECTS OF CARCINOSTATIC AGENT

(75) Inventors: Masahide Ikeguchi, Yonago (JP); Manabu Yamamoto, Yonago (JP); Takayuki Kimura, Sakaiminato (JP); Yasunari Miki, Sakaiminato (JP)

(73) Assignees: National University Corporation Tottori University, Tottori (JP); Marine Products Kimuraya Co., Ltd., Tottori (JP)

( * ) Notice: Subject to any disclaimer, the term of this patent is extended or adjusted under 35 U.S.C. 154(b) by 282 days.

(21) Appl. No.: 13/377,887

(22) PCT Filed: Feb. 22, 2010

(86) PCT No.: PCT/JP2010/052641
§ 371 (c)(1),
(2), (4) Date: Dec. 13, 2011

(87) PCT Pub. No.: WO2011/036904
PCT Pub. Date: Mar. 31, 2011

(65) Prior Publication Data
US 2012/0087943 A1    Apr. 12, 2012

(30) Foreign Application Priority Data

Sep. 28, 2009   (JP) .................... 2009-222553

(51) Int. Cl.
*A61K 36/03* (2006.01)
*A61K 31/737* (2006.01)

(52) U.S. Cl.
CPC .............. *A61K 31/737* (2013.01); *A61K 36/03* (2013.01)
USPC ...................... 424/195.17; 514/54

(58) Field of Classification Search
CPC .... A61K 36/03; A61K 31/737; A61K 31/505
USPC ....................... 424/195.17; 514/54
See application file for complete search history.

(56) References Cited

FOREIGN PATENT DOCUMENTS

| JP | 2001-031575 | | 2/2001 |
| JP | 2004-075595 | | 3/2004 |
| JP | 2004-083558 | | 3/2004 |
| JP | 2007-190004 | A * | 8/2007 |
| JP | 2008-266299 | A * | 11/2008 |

OTHER PUBLICATIONS

English translation of Takayuki (JP 2004-075595)—2004.*
Aprile (Cancer (2008), vol. 112, No. 2, pp. 284-292).*
NCI-CTC manual (National Cancer Institute: Common Toxicity Criteria Manual (Version 2.0. 1999)).*
International Preliminary Report on Patentability and Written Opinion issued Apr. 11, 2012 in International Application No. PCT/JP2010/052641, of which the present application is the national stage.
International Search Report issued Apr. 13, 2010 in International (PCT) Application No. PCT/JP2010/052641, of which the present application is the national stage.
Japanese Journal of Cancer and Chemotherapy, vol. 33, No. 7, 2006, pp. 911-914, with partial English translation.
Japanese Journal of Cancer and Chemotherapy, vol. 33, No. 7, 2006, pp. 904-906, with partial English translation.
Office Action issued Janaury 28, 2014 in Japanese Application No. 2011-532918, with partial English translation.
Ishiwata et al., "Cancer-Suppressing Effect of Acetyl Fucoidan Derived from Okinawa Mozuku (Cladosiphon okamuranus Tokida)", Joumyaku Keityou Eiyou, vol. 22, No. 4, 2007, pp. 489-495, with partial English translation.
Final Rejection issued Jul. 29, 2014 in corresponding Japanese Application No. 2011-532918, with English translation thereof.

* cited by examiner

*Primary Examiner* — Susan Hoffman
(74) *Attorney, Agent, or Firm* — Wenderoth, Lind & Ponack, L.L.P.

(57) ABSTRACT

The present invention provides a side effect inhibitor of drug therapy for colorectal cancer using 5-fluorouracil, comprising fucoidan or a fucoidan-containing material; a method for inhibiting side effects of drug therapy for colorectal cancer using 5-fluorouracil, which comprises administering fucoidan or a fucoidan-containing material to a colorectal cancer patient; and use of fucoidan or a fucoidan-containing material for the production of a side effect inhibitor of drug therapy for colorectal cancer using 5-fluorouracil.

6 Claims, 2 Drawing Sheets

AGENT FOR PREVENTING ADVERSE SIDE EFFECTS OF CARCINOSTATIC AGENT

TECHNICAL FIELD

The present invention relates to a side effect inhibitor of drug therapy for colorectal cancer, which comprises fucoidan or a fucoidan-containing material. Specifically, drug therapy uses 5-fluorouracil such as FOLFOX or FOLFIRI, and side effects include nausea, vomiting, fatigue and the like. This application claims priority on Japanese Patent Application No. 2009-222553, the disclosure of which is incorporated by reference herein.

BACKGROUND ART

Carcinostatic agents such as 5-fluorouracil (5-FU), oxaliplatin, CPT-11 and avastin are now used in various combinations as drug therapy for colorectal cancer. Continuous use for a fixed period of time is indispensable for these carcinostatic agents to exert the effects. However, when these carcinostatic agents are used, various side effects such as fatigue, leucopenia and neurotoxin are exhibited, in addition to digestive symptoms such as nausea, vomiting and diarrhea. Therefore, there are many cases where patients cannot help giving up continuous use of the carcinostatic agent. In the case where the carcinostatic agent cannot be continuously used due to side effects, effects of the carcinostatic agent cannot be exerted, resulting in large disadvantages for patients. That is, in a cancer treatment, countermeasures for side effects of the carcinostatic agent are recognized as urgent issues.

Fucoidan is a generic term of a sulfur-containing polysaccharide containing fucose as a main chain, which exists a lot in seaweeds such as mozuku, root of wakame seaweed ("mekabu", i.e. sporophyl of wakame seaweed), and is distributed as foods. It has recently been proved that fucoidan inhibits proliferation of cultured gastric cancer cells and reduces toxicity of 5-FU as the carcinostatic agent to normal cells (refer to JP-A-2004-75595). However, there has never been reported whether or not fucoidan can actually reduce toxicity of the carcinostatic agent in clinical trial.
Patent Document 1: JP-A-2004-75595

DISCLOSURE OF THE INVENTION

Problems to be Solved by the Invention

It was an object to be achieved by the present invention to inspect whether or not fucoidan can actually inhibit side effects of drug therapy for colorectal cancer in clinical trial, and to use fucoidan for such a purpose.

Means for Solving the Problems

The present inventors have intensively studied so as to achieve the above object and found that fucoidan inhibits side effects such as nausea, vomiting and fatigue in drug therapy for colorectal cancer using 5-FU, and the present invention has been completed.

That is, the present invention provides the followings:
(1) A side effect inhibitor of drug therapy for colorectal cancer using 5-fluorouracil, comprising fucoidan or a fucoidan-containing material;
(2) The side effect inhibitor according to (1), wherein the drug therapy is FOLFOX and/or FOLFIRI;
(3) The side effect inhibitor according to (1) or (2), wherein the side effects are digestive side effects and/or fatigue;
(4) The side effect inhibitor according to any one of (1) to (3), wherein fucoidan is derived from mozuku, or the fucoidan-containing material is mozuku;
(5) A method for inhibiting side effects of drug therapy for colorectal cancer using 5-fluorouracil, which comprises administering fucoidan or a fucoidan-containing material to a colorectal cancer patient;
(6) The method according to (5), wherein the drug therapy is FOLFOX and/or FOLFIRI;
(7) The method according to (5) or (6), wherein the side effects are digestive side effects and/or fatigue;
(8) The method according to any one of (5) to (7), wherein fucoidan is derived from mozuku, or the fucoidan-containing material is mozuku;
(9) Use of fucoidan or a fucoidan-containing material for the production of a side effect inhibitor of drug therapy for colorectal cancer using 5-fluorouracil;
(10) The use according to (9), wherein the drug therapy is FOLFOX and/or FOLFIRI;
(11) The use according to (9) or (10), wherein the side effects are digestive side effects and/or fatigue;
(12) The use according to any one of (9) to (11), wherein fucoidan is administered by the side effect inhibitor in a dose of about 0.5 g to about 5 g (dry weight) per day for adults;
(13) The use according to any one of (9) to (12), wherein fucoidan has a molecular weight of about 300,000;
(14) The use according to any one of (9) to (13), wherein fucoidan is derived from mozuku, or the fucoidan-containing material is mozuku;
(15) The use according to any one of (9) to (14), wherein the drug therapy is FOLFOX and/or FOLFIRI, the side effects are one or more side effects selected from the group consisting of fatigue, loss of appetite, nausea and vomiting, fucoidan is administered by the side effect inhibitor in a dose of about 3 g to about 5 g (dry weight) per day for adults, fucoidan has a molecular weight of about 300,000, and fucoidan is derived from mozuku, or the fucoidan-containing material is mozuku.

The present invention further provides the followings:
(16) A prognosis improving agent of drug therapy for colorectal cancer using 5-fluorouracil, comprising fucoidan or a fucoidan-containing material;
(17) A method for improving prognosis of drug therapy for colorectal cancer using 5-fluorouracil, which comprises administration fucoidan or a fucoidan-containing material to a colorectal cancer patient; and
(18) Use of fucoidan or a fucoidan-containing material for the production of a prognosis improving agent of drug therapy for colorectal cancer using 5-fluorouracil.

Effects of the Invention

According to the present invention, side effects due to drug therapy for colorectal cancer can be inhibited, and thus therapeutic effects on patients are increased and also patients' QOL are also enhanced.

MODE FOR CARRYING OUT THE INVENTION

Figure 1:
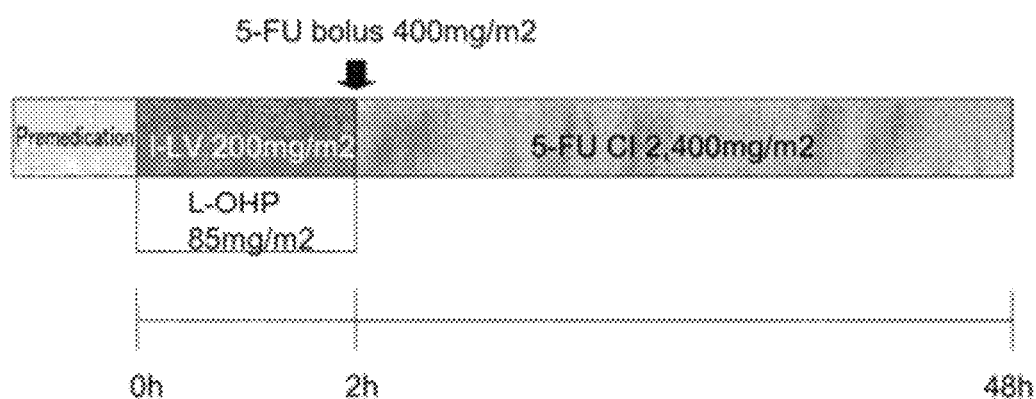
FIG. 1 is a scheme for explaining mFOLFOX6 therapy carried out in Example 1.

The present invention provides a side effect inhibitor of drug therapy for cancer, comprising fucoidan or a fucoidan-containing material. Fucoidan is sulfur-containing polysaccharide found in nature, and a large amount of fucoidan is contained in seaweeds such as mozuku and mekabu. Fucoidan as an active ingredient in the agent of the present invention may be a purified product, and also may be a crude product, for example, an extract from seaweeds such as mozuku.

The fucoidan-containing material as an active ingredient in the agent of the present invention may be any material as long as it contains fucoidan and is nontoxic against human. Examples of preferable fucoidan-containing material in the present invention include seaweeds, particularly brown algae. Examples of the fucoidan-containing brown algae include, but are not limited to, mozuku (Cladosiphon okamuranus (i.e, Okinawa mozuku), Nemacystus decipiens, Tinocladia crazza, Sphaerotrichia divaricata, etc.), mekabu (sporophyl of wakame seaweed), *Undaria pinnatifida* (wakame seaweed), *Eisenia bicyclis* (Sea oak), *Kjellmaniella crassifolia* (Gagome), *Laminaria japonica* (Japanese kelp), *Ecklonia kurome*, *Ecklonia cava* (sea trumpet), *Laminaria angustata* (ribon weed), *Sargassum siliquastrum* (Yoremoku), *Hizuikia fusiforme* (Hiziki), *Sargassum fulvellum* (Gulfweed), *Sargassum patens*, *Sargassum horneri*, *Fucus vesiculosus* (Bladderwrack), *Sargassum thunbergii* and the like. As used herein, the term "mozuku" includes any kind of mozuku, and particularly includes both Cladosiphon okamuranus and Nemacystus decipiens.

The drug therapy for colorectal cancer, for which the agent of the present invention can be applied, may be any drug therapy as long as 5-fluorouracil (5-FU) is used. The drug therapy may be drug therapy using 5-FU alone, and also may be drug therapy using 5-FU in combination with other drugs. Among drug therapy for colorectal cancer which is now often carried out, examples of the combination of 5-FU and other drugs include FOLFOX and FOLFIRI, and modification thereof, and both of them are objects for which the agent of the present invention is applied. FOLFOX is drug therapy using 5-FU, folinic acid and oxaliplatin in combination. FOLFOX includes FOLFOX4, FOLFOX6, modified FOLFOX6 (mFOLFOX6), FOLFOX7 and the like. FOLFIRI is drug therapy using 5-FU, folinic acid and irinotecan in combination. FOLFOX and FOLFIRI may be used alone or used in combination. They are objects for which the agent of the present invention is applied. The drug therapy for colorectal cancer, for which the agent of the present invention can be applied, may be those in which drug therapy such as FOLFOX or FOLFORI is used in combination with the other drug therapy such as avastin. As used herein, drug therapy for colorectal cancer using a prodrug of 5-FU, such as capecitabine is also included in drug therapy using 5-FU.

In the present invention, colorectal cancer may be any kind and includes cecum cancer, transverse colon cancer, ascending colon cancer, descending colon cancer, sigmoid colon cancer, rectal cancer and the like. In the present invention, there is no particular limitation on the nature such as progressive or recurrent property of colorectal cancer.

The agent of the present invention is used in combination with drug therapy for colorectal cancer. The agent of the present invention may be continuously administered from the beginning to the completion of the drug therapy for colorectal cancer, or may be intermittently administered. The agent of the present invention may be administered before the beginning of the drug therapy for colorectal cancer, for example, before several days, before two weeks, before three weeks, and before one month. The agent of the present invention may be administered after completion of the drug therapy for colorectal cancer, thereby reducing the remaining side effects. The agent of the present invention may be administered everyday, or administered at intervals of one to several days. The agent of the present invention may be administered once to several times a day, for example, one to three times. Usually, in case of adults, it is possible to administer fucoidan (in terms of fucoidan dry weight in case of a fucoidan-containing material) in a dose of several 10 mg to several g per day. For example, in case of adults, it is possible to administer fucoidan (dry weight) in a dose of about 10 mg to about 10 g per day, for example, it is possible to administer fucoidan (dry weight) in a dose of about 10 mg to about 0.5 g, about 0.5 g to about 5 g, about 1 g to about 5 g, about 1 g to about 3 g, about 3 g to about 5 g, about 5 g to about 7 g, or about 7 g to about 10 g. Various conditions such as administration timing, administration interval, administration route, dosage and dosage form of the agent of the present invention are not limited to those described above, and a physician can determine or vary the conditions while observing symptoms and side effects of a patient.

The administration route of the agent of the present invention is commonly oral administration. In case of oral administration, the agent of the present invention may be in solid dosage forms such as powders, granules, tablets and capsules; and liquid dosage forms such as solutions, suspensions and extract solutions. The agent of the present invention may be administered in a state of being mixed with ingesta. The agent of the present invention may be in the form of a mozuku processed food. The agent of the present invention may contain, in addition to fucoidan or a fucoidan-containing material, excipients or carriers, or flavoring agents such as vinegar, sugar, soy source and perfume.

There is no particular limitation on the kind of side effects of drug therapy for colorectal cancer to be inhibited by the agent of the present invention. The agent of the present invention particularly has an effect against one or more side effects selected from the group consisting of digestive side effects such as nausea and vomiting; and fatigue such as general malaise.

The present invention provides, in another aspect, a method for reducing side effects of drug therapy for colorectal cancer, which comprises administering fucoidan or a fucoidan-containing material, together with an carcinostatic agent, to a patient. Preferably, drug therapy is FOLFOX and/or FOLFIRI. Preferably, side effects are one or more selected from the group consisting of fatigue, loss of appetite, nausea and vomiting. Preferably, fucoidan is derived from mozuku, or the fucoidan-containing material is mozuku.

The present invention provides, in still another aspect, use of fucoidan or a fucoidan-containing material for the production of a side effect inhibitor of drug therapy for colorectal cancer. Preferably, drug therapy is FOLFOX and/or FOLFIRI. Preferably, side effects are one or more selected from the group consisting of fatigue, loss of appetite, nausea and vomiting. Preferably, fucoidan is derived from mozuku, or the fucoidan-containing material is mozuku.

Reduction of side effects in drug therapy for colorectal cancer increases the number of course of the drug therapy and enhances the therapeutic effect, and thus leading to an improvement in survival rate and QOL of the patient. The target of the number of administration (number of course) of the carcinostatic agent for colorectal cancer using FOLFOX or FOLFIRI is 10 or more. The number of course of 10 or more, which could be achieved by the present invention, shows noticeably remarkable effects of the present invention.

The present invention provides, in yet another aspect, a prognosis improving agent of drug therapy for colorectal cancer using 5-fluorouracil, including fucoidan or a fucoidan-containing material; a method for improving prognosis of drug therapy for colorectal cancer using 5-fluorouracil, which comprises administration fucoidan or a fucoidan-containing material to a colorectal cancer patient; and use of fucoidan or a fucoidan-containing material for the production of a prognosis improving agent of drug therapy for colorectal cancer using 5-fluorouracil.

The present invention will be described below in a detailed and specific manner by way of Examples, but the present invention is not limited to the Examples.

Example 1

A test of a comparison between random groups was carried out, in which persons who were going to be subjected to a treatment with an carcinostatic agent (mFOLFOX6) or persons who were going to be subjected to an a treatment with mFOLFOX6+avastin, among resident or ambulatory patients of Tottori University Faculty of Medicine, Division of Surgical Oncology. They are divided at random into two groups of a fucoidan administration group (N=10) and a non-administration group (N=10). Before the test, explanation about the summary of the present test was made for these patients and the consent in writing was acquired.

Scheme of mFOLFOX6 therapy was as follows (refer to FIG. 1). The treatment was carried out by the following dosing method and dosage for two weeks as one course.

(1) As premedication, a 5-$HT_3$ antagonist and steroid are administered.
(2) L-OHP (oxaliplatin) (85 mg/m$^2$) is dissolved in 250 mL of a 5% glucose solution.
(3) 1-LV (levofolinate) (200 mg/m$^2$) is dissolved in 250 mL of a 5% glucose solution.
(4) The solutions obtained in (2) and (3) are charged in different bags and intravenously injected at the same time over 2 hours using a Y line.
(5) Rapid intravenous injection of 5-FU (400 mg/m$^2$) is carried out within 15 minutes.
(6) Constant intravenous injection of 5-FU (2,400 mg/m$^2$) is carried out over 46 hours.
(7) On 2nd day of a treatment period, an oral steroid is administered for 3 days.

The fucoidan administration group was allowed to ingest one pack (1 pack contains 1,350 mg (dry weight) of fucoidan corresponding to 120 g of mozuku) containing a seaweed food fucoidan (mozuku extract, manufactured by Marine Products Kimuraya, Ltd.) per time three times a day, and the administration period was set at 6 months from the beginning of the treatment with the carcinostatic agent. The above seaweed food fucoidan is prepared in the following manner. Using Okinawa mozuku (Cladosiphon okamuranus) as mozuku, mozuku was suspended in water in the amount which is 1 to 5 times the wet weight of mozuku, followed by acidifying. Fucoidan was eluted by heating at 50° C. or higher and then the precipitate was removed by centrifugal separation. The supernatant was concentrated and desalted by fractionating or dialyzing a low molecular component therefrom to obtain fucoidan (mozuku extract). The low molecular fraction (fraction having a molecular weight of less than about 5,000) was discharged. The weight average molecular weight (Mw) of the obtained fucoidan was about 300,000 in terms of an equivalent molecular weight (measured by a gel filtration method using a high performance liquid chromatograph Prominence manufactured by Shimadzu Corporation and a column for saccharide analysis KS-805 manufactured by Showa Denko K.K.) using a pullulan molecular weight as a standard, and the content of a sulfuric acid group was 13% based on the dry weight of fucoidan. The yield of fucoidan from 100 kg of the wet weight of Cladosiphon okamuranus was 1.125 kg in terms of the dry weight.

With respect to the following items:
1. loss of appetite, 2. nausea, vomiting, 3. diarrhea, 4. stomatitis, 5. neurological symptom, 6. fatigue, and 7. cytopenia, rating was carried out in accordance with NCI-CTC to obtain scores. The evaluation was carried out every 3 months during the administration period. The number of analyzable patients in the above test was 9 in the fucoidan administration group, while the number of analyzable patients was 8 in the fucoidan non-administration group.

A comparison in total scores obtained in accordance with NCI-CTC was made between the fucoidan administration group and the fucoidan non-administration group. The results are shown in Table 1.

TABLE 1

| Items | Fucoidan administration group (N = 9) | Fucoidan non-administration group (N = 8) |
|---|---|---|
| 1. Loss of appetite | 7 | 9 |
| 2. Nausea, Vomiting | 6 | 10 |
| 3. Diarrhea | 1 | 1 |
| 4. Stomatitis | 7 | 2 |
| 5. Neurological symptom | 6 | 3 |
| 6. Fatigue | 5 | 13 |
| 7. Cytopenia | 13 | 8 |

In the fucoidan administration group, a reduction in fatigue was remarkable. In the fucoidan administration group, a reduction in nausea and vomiting was also confirmed The number of cases of moderate (score of 2 in accordance with NCI-CTC) or higher disease are summarized in Table 2.

TABLE 2

| Items | Fucoidan administration group (N = 9) | Fucoidan non-administration group (N = 8) | P |
|---|---|---|---|
| 1. Loss of appetite | 1 | 2 | 0.453 |
| 2. Nausea, Vomiting | 0 | 3 | 0.043 |
| 3. Diarrhea | 0 | 0 | — |
| 4. Stomatitis | 3 | 0 | 0.072 |
| 5. Neurological symptom | 0 | 0 | — |
| 6. Fatigue | 0 | 5 | 0.005 |
| 7. Cytopenia | 4 | 3 | 0.772 |

It was confirmed that fucoidan administration is also effective to reduce fatigue of moderate or higher disease, and to reduce loss of appetite, nausea and vomiting.

Figure 2:
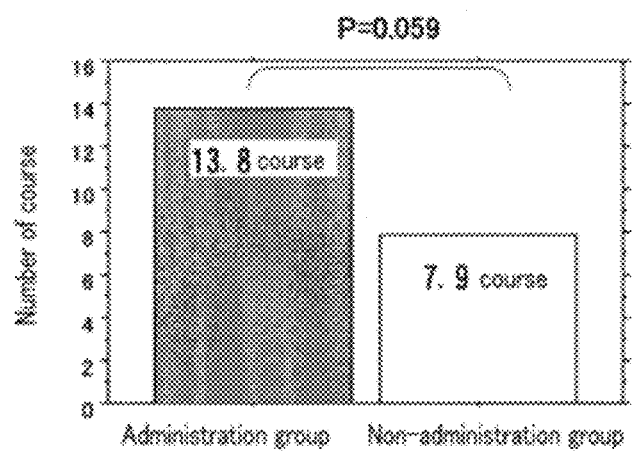
FIG. 2 is a graph showing a comparison in administration course between a fucoidan administration group and a non-administration group.

Under the above test conditions, the treatment was continued and a comparison in the number of administration of the carcinostatic agent (administration course) was made between a fucoidan administration group and a non-administration group (FIG. 2). The average course number was 7.9 (SE 2.7) in the Fucoidan non-administration group, whereas, the average course number was 13.8 (SE 0.3) in the fucoidan administration group, and thus it became possible to remarkable increase in the course number by fucoidan administration.

Figure 3:
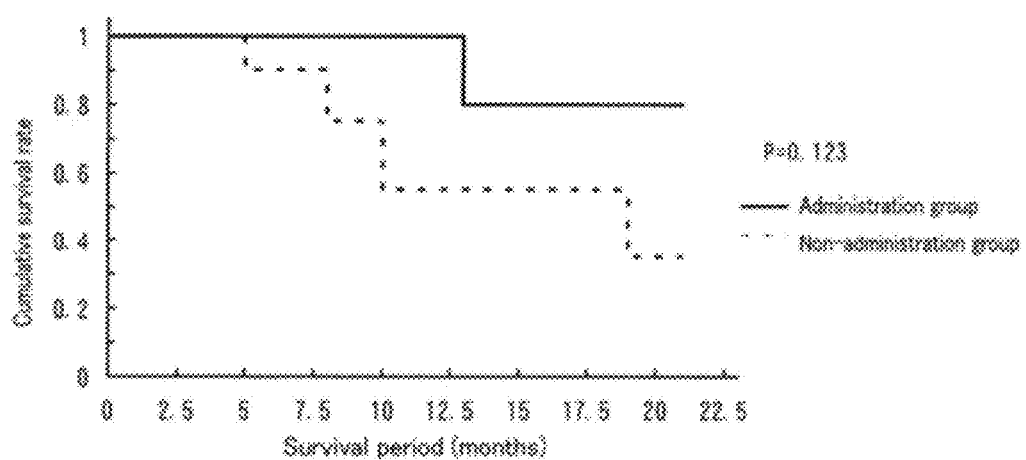
FIG. 3 is a graph showing a comparison in a survival rate between a fucoidan administration group (solid line) and a non-administration group (broken line).

Furthermore, the survival rate under the above test conditions was also examined (FIG. 3). Using the Kaplan-Meier method, a test of the survival rate was carried out by the log-rank test. In the fucoidan administration group, an improvement in the survival rate was confirmed as compared with the fucoidan non-administration group.

As is apparent from the above results, fucoidan is effective to reduce digestive side effects such as nausea and vomiting as well as side effects such as fatigue involved in drug therapy containing 5-FU such as FOLFOX or FOLFIRI in the colorectal cancer case. As a result, the number of treatment course can be increased and also prognosis is satisfactory.

INDUSTRIAL APPLICABILITY

The present invention can be utilized in drug pharmaceutical industry, food manufacturing industry and the like.

The invention claimed is:

1. A method for inhibiting side effects of drug therapy for colorectal cancer using 5-fluorouracil, which comprises administering isolated fucoidan to a colorectal cancer patient, wherein the side effect of the colorectal cancer patient is fatigue having a moderate score of 2 or higher, in accordance with NCI-CTC, and
wherein the isolated fucoidan has a molecular weight of about 300,000.

2. The method according to claim 1, wherein the drug therapy is FOLFOX and/or FOLFIRI.

3. The method according to claim 1, wherein the isolated fucoidan is derived from mozuku.

4. The method according to claim 1, wherein the isolated fucoidan is contained in a side effect inhibitor and is administered in a dose of about 0.5 g to about 5 g, based on dry weight, per day for adults.

5. The method according to claim 1, wherein the drug therapy is FOLFOX and/or FOLFIRI,
the isolated fucoidan is contained in a side effect inhibitor and is administered in a dose of about 3 g to about 5 g, based on dry weight, per day for adults,
and the isolated fucoidan is derived from mozuku.

6. The method according to claim 1, wherein the isolated fucoidan is derived from Okinawa mozuku.

* * * * *